(12) United States Patent
Moon

(10) Patent No.: US 10,130,322 B2
(45) Date of Patent: Nov. 20, 2018

(54) MAMMOGRAPHY DEVICE AND METHOD OF CONTROLLING POSITION ALIGNMENT THEREOF

(71) Applicant: GENERAL ELECTRIC COMPANY, Schenectady, NY (US)

(72) Inventor: Jin Young Moon, Seoul (KR)

(73) Assignee: General Electric Company, Schenectady, NY (US)

( * ) Notice: Subject to any disclaimer, the term of this patent is extended or adjusted under 35 U.S.C. 154(b) by 25 days.

(21) Appl. No.: 14/781,269

(22) PCT Filed: Sep. 30, 2013

(86) PCT No.: PCT/KR2013/008765
§ 371 (c)(1),
(2) Date: Sep. 29, 2015

(87) PCT Pub. No.: WO2014/157793
PCT Pub. Date: Oct. 2, 2014

(65) Prior Publication Data
US 2016/0051213 A1     Feb. 25, 2016

(30) Foreign Application Priority Data

Mar. 29, 2013  (KR) .................. 10-2013-0034343

(51) Int. Cl.
*A61B 6/00* (2006.01)
*A61B 6/04* (2006.01)
*A61B 6/03* (2006.01)

(52) U.S. Cl.
CPC ............... *A61B 6/502* (2013.01); *A61B 6/03* (2013.01); *A61B 6/04* (2013.01); *A61B 6/0407* (2013.01);

(Continued)

(58) Field of Classification Search
CPC ... A61B 6/0407; A61B 6/0414; A61B 6/0421; A61B 6/44; A61B 6/4405; A61B 6/4435;
(Continued)

(56) References Cited

U.S. PATENT DOCUMENTS 4,910,756 A   3/1990  Mikkonen et al.
5,050,197 A *  9/1991  Virta ..................... A61B 6/0414
                                            378/210

(Continued)

FOREIGN PATENT DOCUMENTS

CN    201977812 U    9/2011
JP    H01-209047 A   8/1989
(Continued)

OTHER PUBLICATIONS

International Search Report for PCT/KR2013/008765 dated Jan. 10, 2014.

(Continued)

*Primary Examiner* — Allen C. Ho
(74) *Attorney, Agent, or Firm* — Global Patent Operation; Marc A. Vivenzio

(57) ABSTRACT

Disclosed herein is a mammography device for X-ray photographing an object to be inspected. The mammography device includes: a device body movable in a vertical axis direction and rotatable around a first horizontal axis; a generator fixed to one end portion of the device body; a support part for the object including a detector; a first moving unit moving the device body in the vertical axis direction; a rotating unit rotating the device body around the first horizontal axis; and a controller controlling the first moving unit and the rotating unit, wherein the controller performs a control so that the rotating unit rotates the device body and the first moving unit moves the device body together with the rotation of the device body in order to (Continued)

position a center of an upper surface of the support part for the object on the same horizontal surface.

4 Claims, 5 Drawing Sheets

(52) U.S. Cl.
CPC .............. *A61B 6/0421* (2013.01); *A61B 6/44* (2013.01); *A61B 6/4405* (2013.01); *A61B 6/4435* (2013.01); *A61B 6/4441* (2013.01); *A61B 6/4452* (2013.01); *A61B 6/4476* (2013.01); *A61B 6/54* (2013.01); *A61B 6/542* (2013.01); *A61B 6/545* (2013.01); *A61B 6/0414* (2013.01)

(58) Field of Classification Search
CPC ..... A61B 6/4441; A61B 6/4476; A61B 6/502; A61B 6/54; A61B 6/542; A61B 6/545; A61B 6/4452
USPC ............................................. 378/37, 91, 205
See application file for complete search history.

(56) References Cited

U.S. PATENT DOCUMENTS

| | | | | |
|---|---|---|---|---|
| 5,099,503 A * | 3/1992 | Strömmer | ................ | H05G 1/64 378/208 |
| 5,170,420 A * | 12/1992 | Warden | .................. | A61B 6/447 378/196 |
| 5,415,169 A * | 5/1995 | Siczek | ................. | A61B 6/0435 600/427 |
| 5,848,123 A * | 12/1998 | Strömmer | .......... | H04N 5/37206 378/98.8 |
| 5,872,364 A * | 2/1999 | Strömmer | ................ | A61B 6/14 250/370.09 |
| 6,999,554 B2 * | 2/2006 | Mertelmeier | ........ | A61B 6/0414 378/196 |
| 7,003,073 B2 * | 2/2006 | Andreasson | ........... | A61B 6/502 378/177 |
| 7,039,155 B2 * | 5/2006 | Akagi | .................. | A61B 6/4283 378/165 |
| 7,073,940 B2 * | 7/2006 | Saladin | .................... | A61B 6/56 378/193 |
| 7,573,977 B2 * | 8/2009 | Tsujita | ..................... | A61B 6/56 378/197 |
| 7,885,379 B2 * | 2/2011 | Meer | ...................... | A61B 6/502 378/37 |
| 7,940,890 B1 * | 5/2011 | Linev | ...................... | A61B 6/06 378/146 |
| 7,945,020 B2 * | 5/2011 | Jan | ........................ | A61B 6/4258 378/209 |
| 7,957,503 B2 * | 6/2011 | Kobayashi | .......... | A61B 6/0414 378/209 |
| 8,031,834 B2 * | 10/2011 | Ludwig | ................ | A61B 6/025 378/22 |
| 8,406,846 B2 * | 3/2013 | Yoshizawa | .......... | A61B 5/0091 600/407 |
| 8,467,495 B2 * | 6/2013 | Okada | .................... | A61B 6/022 378/151 |
| 8,475,376 B2 * | 7/2013 | Mikami | ............... | A61B 6/0414 600/407 |
| 8,532,253 B2 * | 9/2013 | Virta | .................... | A61B 6/0457 378/37 |
| 8,553,837 B2 * | 10/2013 | Johansson | .............. | A61B 6/025 378/22 |
| 8,787,522 B2 * | 7/2014 | Smith | .................... | A61B 6/025 378/20 |
| 8,792,617 B2 * | 7/2014 | Baetz | ................... | A61B 6/4035 378/16 |
| 8,825,135 B2 * | 9/2014 | Okada | ...................... | A61B 6/00 600/407 |
| 8,838,207 B2 * | 9/2014 | Nakayama | ........... | A61B 6/0414 378/147 |
| 8,848,865 B2 * | 9/2014 | Nakayama | ........... | A61B 6/0414 378/37 |
| 8,918,932 B2 * | 12/2014 | Taku | .................... | A61B 5/0091 378/209 |
| 9,060,739 B2 * | 6/2015 | Kim | ........................ | A61B 6/035 |
| 9,282,942 B2 * | 3/2016 | Mertelmeier | .......... | A61B 6/502 |
| 9,420,982 B2 * | 8/2016 | Kim | ........................ | A61B 6/4233 |
| 9,451,923 B2 * | 9/2016 | Hemmendorff | ....... | A61B 6/4452 |
| 9,460,822 B2 * | 10/2016 | Danielsson | .............. | A61B 6/06 |
| 9,492,128 B2 * | 11/2016 | Lee | ........................ | A61B 6/0414 |
| 9,510,794 B2 * | 12/2016 | Kuwabara | ................ | G01T 1/24 |
| 9,597,040 B2 * | 3/2017 | Hemmendorff | ........ | A61B 6/025 |
| 9,655,577 B2 * | 5/2017 | Choi | ...................... | A61B 6/025 |
| 9,883,846 B2 * | 2/2018 | Son | ...................... | A61B 6/4435 |
| 2003/0198315 A1 | 10/2003 | Andreasson et al. | | |
| 2005/0168826 A1 | 8/2005 | Koulikov et al. | | |
| 2010/0067648 A1 | 3/2010 | Kojima | | |

FOREIGN PATENT DOCUMENTS

| | | | |
|---|---|---|---|
| JP | H04-317632 | A | 11/1992 |
| JP | H06-154197 | A | 6/1994 |
| JP | 2003-310594 | A | 11/2003 |
| JP | 2007-097827 | A | 4/2007 |
| JP | 2000-207680 | A | 9/2009 |
| JP | 2010-088929 | A | 4/2010 |
| JP | 2010-110571 | A | 5/2010 |
| KR | 10-2013-0003271 | A | 1/2013 |

OTHER PUBLICATIONS

Extended European Report for European Application No. 13880690.6 dated Mar. 10, 2016.

Machine translation and Decision to Grant issued in connection with corresponding JP Application No. 2016-505371 dated Apr. 25, 2017.

Machine Translation and First Office Action and Search issued in connection with corresponding CN Application No. 201380076468.2 dated Aug. 28, 2017.

* cited by examiner

[Fig. 1]
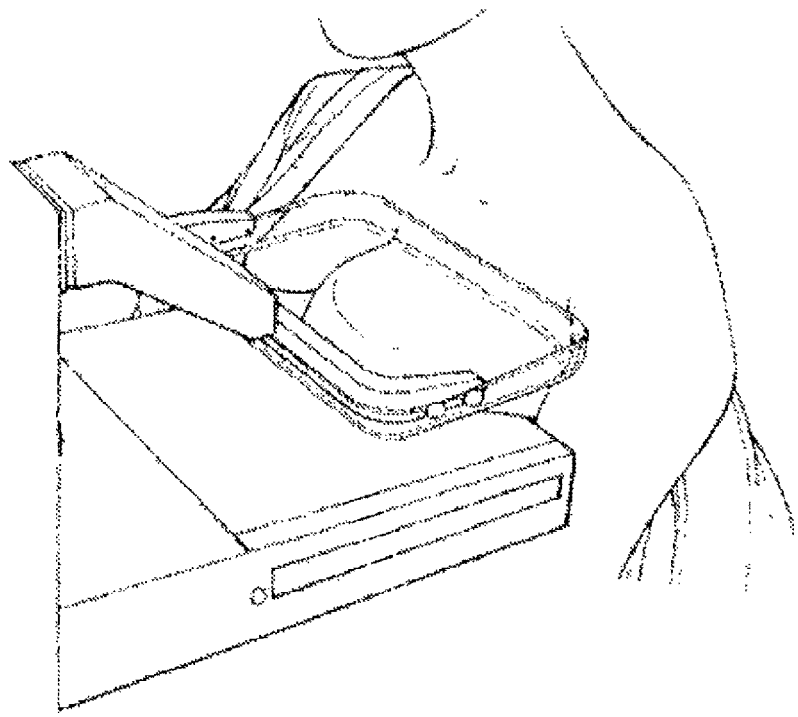
[Fig. 2]
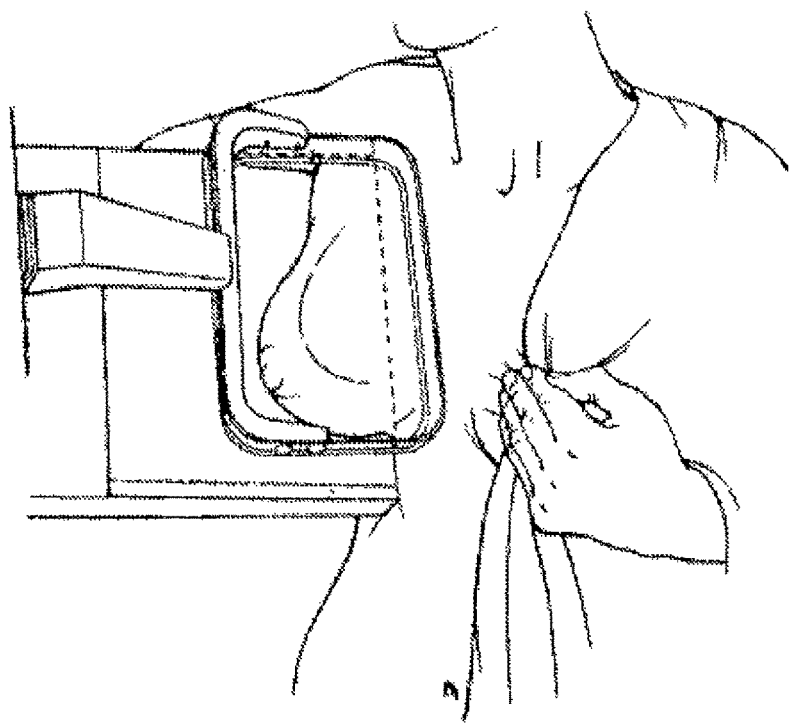

[Fig. 3]
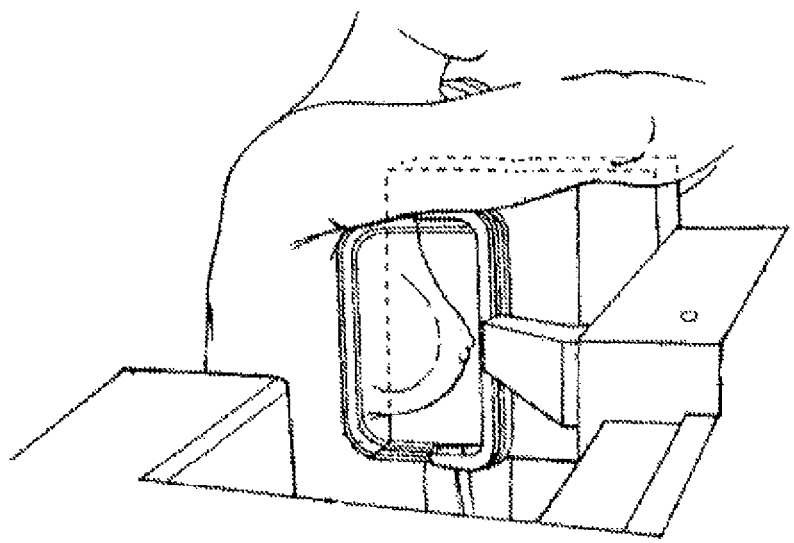
[Fig. 4]
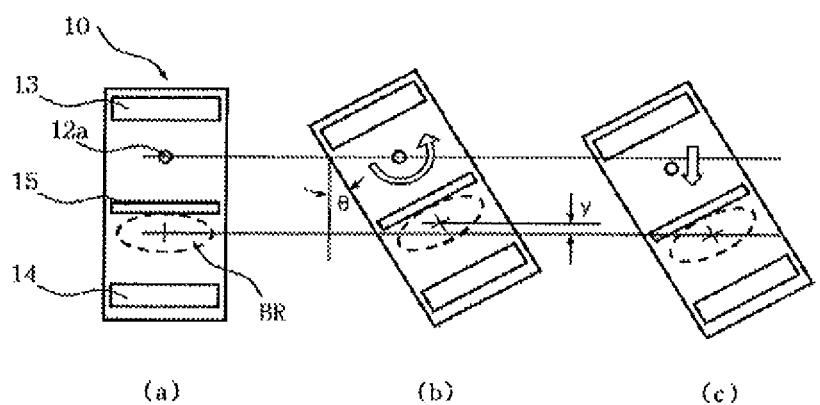
(a)　　　　(b)　　　　(c)

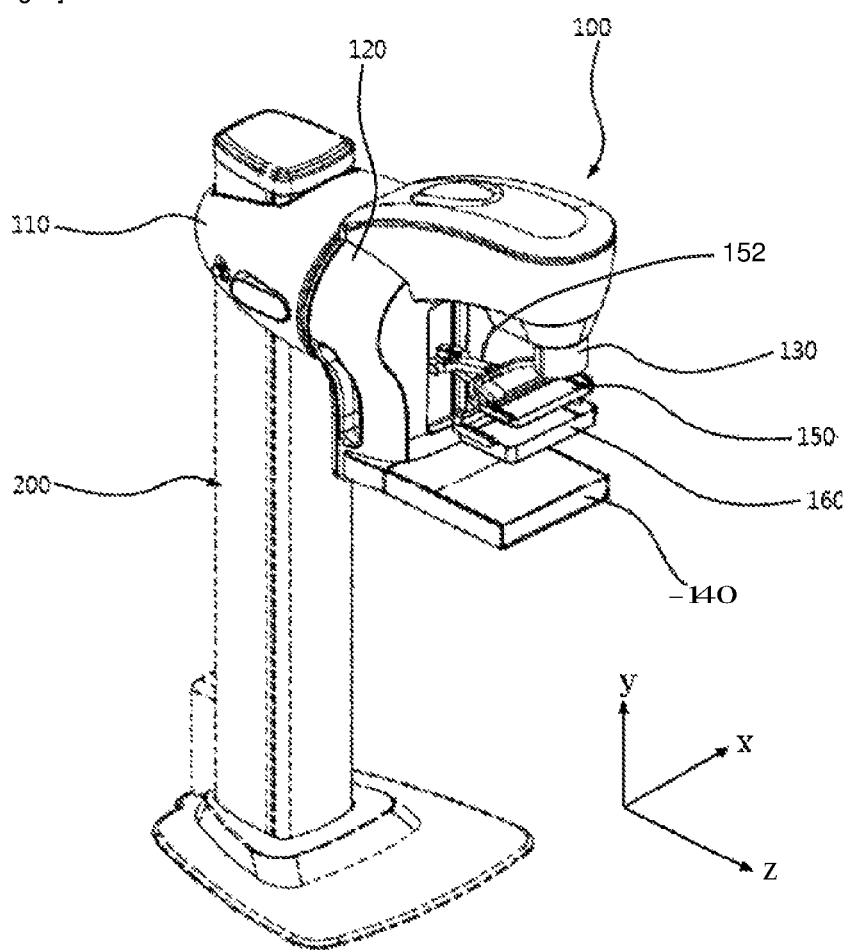
[Fig. 5]

[Fig. 6]
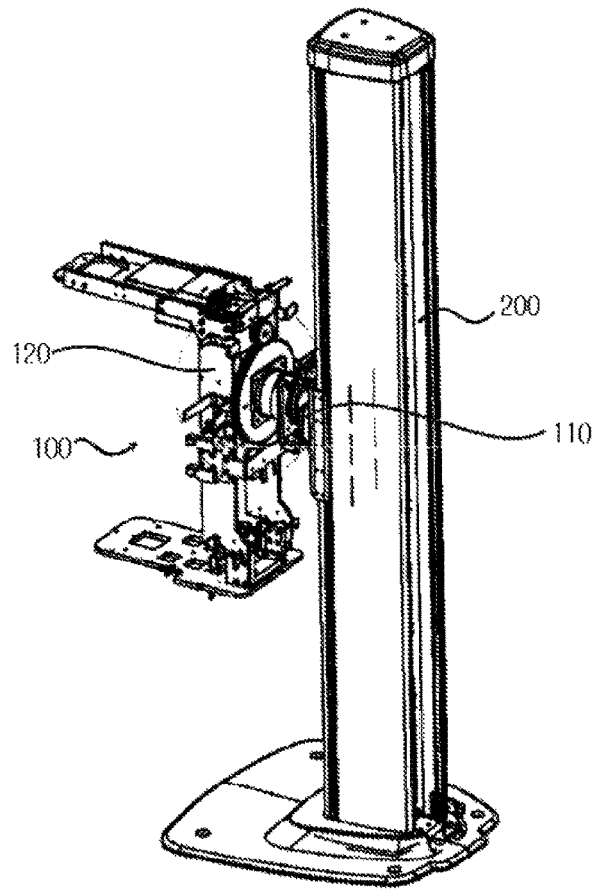
[Fig. 7]
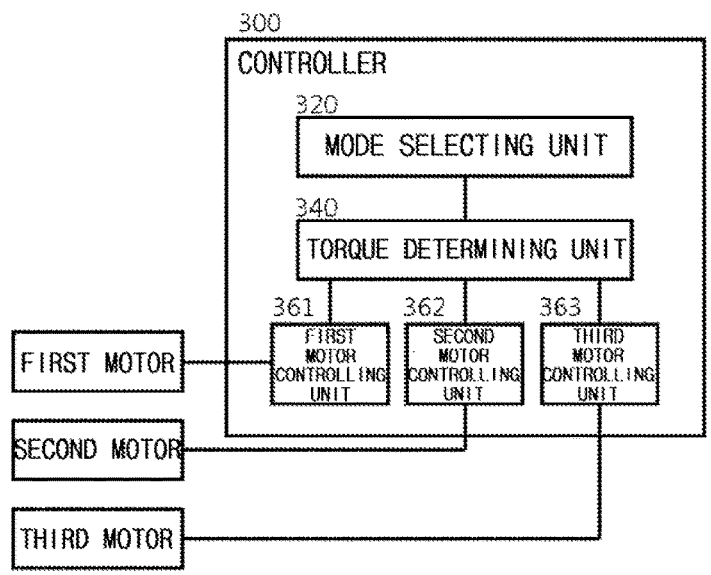

[Fig. 8]
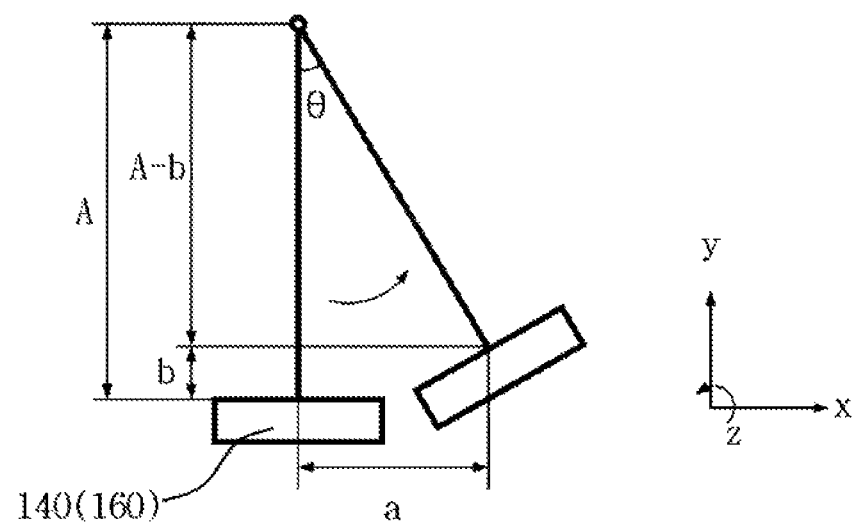

MAMMOGRAPHY DEVICE AND METHOD OF CONTROLLING POSITION ALIGNMENT THEREOF

TECHNICAL FIELD

The present invention relates to a mammography device for X-ray photographing a beast and a method of controlling position alignment thereof, and more particularly, to a mammography device in which an inspection unit may rapidly move to and be aligned with a position appropriate for a body shape of a subject, and a method of controlling position alignment thereof.

The present invention is derived from research performed as a part of nano-material based multi X-ray source and tomography image system technology development of the Ministry of Knowledge Economy [Project Management Number: 10037414, Project Name: Nano-material Based Multi X-ray Source and Tomography Image System Technology Development].

BACKGROUND ART

An X-ray generally indicates a short, wavelength electromagnetic wave having a wavelength of 0.01 nm to 10 nm and a frequency of $30 \times 10^{15}$ Hz to $30 \times 10^{18}$ Hz. X-ray photographing is one of radiographics of projecting and displaying an inner portion of an object to be inspected by high penetration power of the X-ray. As well-known, the X-ray involves an attenuation phenomenon depending on a material, a density, and a thickness of an object, such as Compton scattering, a photoelectric effect, or the like, during a process in which it is transmitted through the object. Therefore, the X-ray photographing projects and displays the inner portion of the object to be inspected on the basis of an attenuation amount of the X-ray accumulated during a process in which the X-ray passes through the object to be inspected. To this end, a dedicated X-ray system is used.

Recently, an X-ray image technology has been rapidly evolved as a digital X-ray image technology having various advantages such as a relatively high resolution, a wide dynamic area, easy generation of an electrical signal, simple processing and storing of data, and the like, instead of a traditional analog scheme using a film while being grafted onto a semiconductor field. A digital based image technology strongly reflects a clinically environmental demand such as an early diagnosis of a disease on the basis of excellent diagnosis ability of a digital image.

Therefore, a "digital mammography", which is a breast dedicated X-ray photographing technology capable of detecting a lesion and micro-calcification for detection and an early diagnosis of a breast cancer by representing an internal structure of the breast corresponding to an object to be inspected as a high resolution image, using unique biological tissue contrast capability of the X-ray, has been introduced. The digital mammography has been rapidly spread due to unique characteristics such as image enlargement, a decrease in the number of times of photographing, an increase in a resolution, and minimization of exposure through adjustment, of a luminance and a contrast ratio together with various advantages of the digital X-ray image technology.

A general mammography device mainly includes a support, column having a lower end portion fixed to a bottom and having a vertical column shape and a C-arm or a device body installed on the support column so as to ascend or descend in a vertical direction and generally having a C shape or a shape similar to the C shape in which a central portion thereof is configured to be rotatable around a horizontal axis. A generator irradiating an X-ray toward a lower end portion of the device body is mounted at an upper end portion of the device body, and a detector facing the generator is mounted at the lower end portion of the device body. A pressing pad that vertically and linearly reciprocates along an inner surface of the device body is installed between the generator and the detector.

In the mammography device as described above, when a subject is in a standing or sitting state at a photographing position, the device body ascends or descends and rotates with respect to the support column, such that a height and an angle of the device body are adjusted so that, a breast of the subject is put at a target position on the detector. Then, the pressing pad moves toward the detector to press the breast. In this state, the generator irradiates the X-ray toward the breast and the detector, and the detector positioned behind the breast receives the X-ray passing through the breast to obtain an image.

That is, the detector generates an electric signal for each position that is in proportion to an amount of incident X-ray, and reads the electrical signal and position information and processes the read electrical signal and position information by an image processing algorithm, thereby making it possible to obtain an X-ray image of the breast for a corresponding angle. Then, the above-process is repeated while rotating the generator and the detector with the breast interposed therebetween, whereby the mammography device may obtain high resolution images for the breast of the subject at various angles.

In a general mammography device having the above-mentioned photographing principle, a critical driving mechanical for minimizing discomfort of the subject and obtaining a high quality X-ray image is a pressing operation of the pressing pad and ascending or descending and rotating operations of the device body. Particularly, since the pressing pad applies direct pressure to the breast at the time of X-ray photographing, it is directly associated with pain and discomfort felt by the subject, and since the device body determines an accurate photographing position through ascent or descent and rotation, it is directly associated with quality of the X-ray image.

Here, the pressing pad presses the breast in order to photograph the breast in a state in which the breast, is pressed for the purpose of separating a lump (a lesion or a portion at which the possibility of micro-calcification is high) looking like being overlapped with a mammary gland, or the like, from the mammary gland. In order to accurately detect the lesion or the micro-calcification, the breast is generally photographed at various angles.

FIGS. 1 to 3 are schematic views illustrating a standard photographing method of a mammography device, wherein FIG. 1 illustrates a craniocaudal view (CC), and FIGS. 2 and 3 illustrate a mediolateral oblique view. FIGS. 4A to 4C are schematic views illustrating an operation mechanism of a general mammography photographing unit.

As illustrated in FIGS. 1 to 3, in the case of a standard mode, CC and MLO are performed on each of left and right breasts. For example, at least three views including RCC and RMLO are performed on the right breast, and at least three views including LCC and LMLO are performed on the left breast. In order to perform these views, the photographing unit of the mammography device should rotate at a corresponding angle.

Referring to FIGS. 4A to 4C, in a mammography device according to the related art, a shaft 12a of a device body 10 including a photographing unit is generally positioned in a state in which it is eccentric upwardly from the center of the device body 10 due to the center of gravity, or the like. Therefore, the device body 10 presses a breast BR, which is an object to be inspected, between a pressing pad 15 and a detector 14 at a position of FIG. 4A to perform the CC by a generator 13 and the detector 14. Then, in order to perform the MLO, the device body 10 should rotate at a desired angle θ as illustrated in FIG. 4B and then descend again by y so as to be appropriate for a height of the breast as illustrated in FIG. 4C. That is, the device body 10 performs a two-stage operation of rotation and descent.

In the mammography device according to the related art described above, a position and an angle of the mammography device are manually adjusted depending on a body shape (a height of a subject, a position of a breast, and the like) of a subject at the time of performing standard photographing, and linear movement and rotation of the device body are generally controlled separately, such that a rapid operation is not provided. For example, as described above, a height of the photographing unit is changed by rotation of the device body at the time of performing the MLO after performing the CC or at the time of performing the CC after performing the MLO. Then, the photographing unit should descend or ascend by the height changed by the rotation. Therefore, an accuracy may be decreased. Further, the subject should move backward from the mammography device in order to allow the device body to ascend or descend, and again enter a photographing position after the height is adjusted. For this reason, a photographing time of the mammography device becomes long, such that fatigue of the subject and an inspector is increased. In addition, it is difficult to obtain a bilaterally uniform photographing result due to a manual manipulation, such that a photographing accuracy is decreased.

DISCLOSURE

Technical Problem

Therefore, the present invention has been made to solve the above-mentioned problems of the related art. An object of the present invention is to provide a mammography device capable of being driven in a time as short as possible at the time of performing X-ray photographing at various angles and being easily aligned with a position appropriate for a body shape (a height of a subject or a height of a breast) of a subject, and a method of controlling position alignment thereof.

Technical Solution

According to an aspect of the present invention, there is provided a mammography device including: a device body movable in a vertical axis direction and rotatable around a first horizontal axis so as to photograph an object to be inspected by a craniocaudal view and a mediolateral oblique view; a generator fixed to one end portion of the device body and irradiating an X-ray; a support part for the object to be inspected including a detector fixed to the other end portion of the device body and facing the generator; a first moving unit moving the device body in the vertical axis direction; a rotating unit rotating the device body around the first horizontal axis; and a controller controlling the first moving unit and the rotating unit, wherein the controller performs a control so that the rotating unit rotates the device body and the first moving unit moves the device body together with the rotation of the device body in order to position a center of an upper surface of the support part for the object to be inspected on the same horizontal surface.

The mammography device may further include a second moving unit moving the device body in a second horizontal axis direction perpendicular to the first horizontal axis, wherein the device body is movable in the second horizontal axis direction and a second moving unit is controlled by the controller, and the controller performs a control so that the rotating unit rotates the device body and the first and second moving units move the device body together with the rotation of the device body in order not to move the center of the upper surface of the support part for the object to be inspected.

According to another aspect of the present invention, there is provided a method of controlling position alignment of a mammography device, including: providing the mammography device including a device body movable in a vertical axis direction and rotatable around a first horizontal axis so as to photograph an object to be inspected by a craniocaudal view and a mediolateral oblique view, a generator fixed to one end portion of the device body and irradiating an X-ray, and a support part for the object to be inspected including a detector fixed to the other end portion of the device body and facing the generator; and rotating the device body around the first horizontal axis and moving the device body in the vertical axis direction together with the rotation of the device body in order to position a center of an upper surface of the support part for the object to be inspected on the same horizontal surface.

The device body may be movable in a second horizontal axis direction perpendicular to the first horizontal axis, and the rotating of the device body around the first horizontal axis and the moving of the device body in the vertical axis direction together with the rotation of the device body may include rotating the device body around the first horizontal axis and moving the device body in the vertical axis direction and the second horizontal axis direction together with the rotation of the device body in order not to move the center of the upper surface of the support part for the object to be inspected.

Advantageous Effects

As described above, in the mammography device and the method of controlling position alignment thereof according to an exemplary embodiment of the present invention, rotation and ascent and descent operations of a photographing unit are performed together with each other and are automatically performed simultaneously at the time of performing X-ray photographing at various angles to maximally decrease movement of a subject during position alignment of the photographing unit, thereby making it possible to maximally shorten a driving and photographing time of the mammography device. The time is shortened as described above, such that fatigue and discomfort of the subject and an inspector may be minimized.

In addition, the rotation and ascent and descent operations of the photographing unit are automatically performed simultaneously, such that an accurate bilaterally uniform photographing result may be obtained, thereby making it possible to accurately read a lesion, micro-calcification, or the like.

DESCRIPTION OF DRAWINGS

FIGS. 1 to 3 are schematic views illustrating a standard photographing method of a mammography device, wherein FIG. 1 is a view illustrating a craniocaudal view (CC), and FIGS. 2 and 3 are views illustrating a mediolateral oblique view.

FIGS. 4A to 4C are schematic views illustrating an operation mechanism of a general mammography photographing unit.

FIG. 5 is a perspective view illustrating an entire configuration of a mammography device according to an exemplary embodiment of the present invention.

FIG. 6 is a partial perspective view of a device body and a support column of the mammography device according to an exemplary embodiment of the present invention.

FIG. 7 is a schematic view illustrating a controller of the mammography device according to an exemplary embodiment of the present invention.

FIG. 8 is a view for describing an operation of the mammography device according to an exemplary embodiment of the present invention.

BEST MODE

Additional objects, features, and advantages of the present invention may be more clearly understood from the following detailed description and the accompanying drawings. Prior to a detailed description of the present invention, the present invention may be variously modified and altered and have several exemplary embodiments. Examples described below and illustrated in the drawings are not to limit the present invention to specific exemplary embodiments. In addition, various modifications, alterations, and amendments may be made in the scope of the following claims, and it may be understood that these modifications, alterations, and amendments fall within the scope of the present invention.

It is to be understood that when one element is referred to as being "connected to" or "coupled to" another element, it may be connected directly to or coupled directly to another element or be connected indirectly to or coupled indirectly to another element with the other element intervening therebetween. On the other hand, it is to be understood that when one element is referred to as being "connected directly to" or "coupled directly to" another element, it may be connected to or coupled to another element without the other element intervening therebetween.

Terms used in the present specification are used only in order to describe specific exemplary embodiments rather than limiting the present invention. Singular forms include plural forms unless the context clearly indicates otherwise. It will be further understood that terms "include", "have", or the like, used in the present specification are to specify the presence of features, numerals, steps, operations, components, parts mentioned in the present specification, or a combination thereof, but do not preclude the presence or addition of one or more other features, numerals, steps, operations, components, parts, or a combination thereof.

A term "part", "-er/or", "unit", "module", or the like, described in the present specification means a processing unit of at least one function or operation and may be implemented by hardware or software or a combination of hardware and software.

In describing the present invention with reference to the accompanying drawings, the same components will be denoted by the same reference numerals, and an overlapped description therefor will be omitted. When it is decided that a detailed description for the known art related to the present invention may unnecessarily obscure the gist of the present invention, the detailed description will be omitted.

Hereinafter, a digital mammography device according to an exemplary embodiment of the present invention will be described in detail with reference to the accompanying drawings. Although a digital type mammography device has been described as an example of a "mammography device" in the present specification, the present invention is not limited thereto, but may also be applied to an analog type mammography device.

FIG. 5 is a perspective view illustrating an entire configuration of a mammography device according to an exemplary embodiment of the present invention, and FIG. 6 is a partial perspective view of a device body and a support column of the mammography device according to an exemplary embodiment of the present invention.

As illustrated in FIGS. 5 and 6, the mammography device according to an exemplary embodiment of the present invention is configured to include a device body 100 including basic components for X-ray photographing and a support column 200 to which the device body 100 is connected to be vertically movable.

The support column 200 has a vertical column shape and basically serves to support the device body 100. The support column 200 may have a lower end portion mounted on a base rail (not illustrated) in an x axis direction in FIG. 5 to be movable along an x axis. The base rail includes a support column moving unit (not illustrated), and the support column moving unit may linearly move the support column 200 in the x axis direction. To this end, the support column moving unit may include a first motor and any one of a rack/pinion, a belt, and a ball screw, which is a means for converting rotation of the first motor into linear movement. Since these components are a technology well-known to those skilled in the art, a detailed description therefor will be omitted. Meanwhile, the support column 200 provides a vertical axis to the device body 100 so that the device body 100 may ascend or descend in a vertical length direction (y axis direction in FIG. 5) while supporting the device body 100. In addition, the support column 200 includes a device body ascending or descending unit for vertically moving the device body 100 (more specifically, a support column connection part 110 of the device body 100). The device body ascending or descending unit includes a second motor and a means for converting rotation of the second, motor into linear movement, which are substantially the same as those of support column moving unit except for a driving direction.

The device body 100 has an arc shape in which upper and lower (both) end portions thereof face each other, and is called a C arm since it generally has a C shape or a shape similar to the C shape. The device body 100 includes the support column connection part 110 connected to the support column 200 so as to ascend or descend in the vertical direction and a vertical connection part 120 connected to the support column connection part 110 so as to be rotatable around the support column connection part 110. The device body 100, which is a photographing unit, includes a generator 130 mounted at one end portion (for example, an upper end portion in the present exemplary embodiment) of the vertical connection part 120 of the device body 100 and irradiating an X-ray toward the other end portion (for example, a lower end portion in the present exemplary embodiment) of the vertical connection part 120 facing one end portion of the vertical connection part 120, a detector 140 mounted at the other end portion of the vertical connection part 120 and facing the generator 130, and a pressing pad 150 linearly reciprocating between the generator 130 and the detector 140 along an inner surface of the device body 100 and having a plate shape. An object to be inspected is positioned between the pressing pad 150 and the detector 140, and X-ray photographing is performed on the object to be inspected. Alternatively, an inspection plate 160 may be selectively installed between the pressing pad 150 and the detector 140, the object to be inspected may be positioned between the pressing pad 150 and the inspection plate 160, and X-ray photographing may be performed on the object to be inspected. That is, in the case in which the inspection plate 160 is not present, the detector 140 serves as a support part for the object to be inspected, and in the case in which the inspection plate 160 is present, the inspection plate 160 serves as a support part, for the object to be inspected.

The vertical connection part 120 is connected to the support column connection part 110 so as to be rotatable around a horizontal axis (z axis of FIG. 5) so that a breast may be photographed by a mediolateral oblique view, and a device body rotating unit (not illustrated) for rotating the vertical connection part 120 as described above is installed at the support column connection part 110. The device body rotating unit may include a third motor and a series of gear trains. Since these components also are a technology well-known to those skilled in the art, a detailed description therefor will be omitted.

The vertical connection part 120 basically includes upper and lower (both) end portions at which the generator 130 and the detector 140 are mounted, respectively, and a column connecting the upper and lower (both) end portions to each other. The pressing pad 150 is slidingly mounted on the column of the vertical connection part 120, and a driving means for vertically moving the pressing pad 150 is installed at one side of the vertical connection part 120. The breast positioned on the detector 140 or on the inspection plate 160 in some cases is pressed by the above-mentioned vertical movement of a pressing pad support part 152 and the pressing pad 150 connected to the pressing pad support part 152.

The generator 130 mounted at an upper end portion of the device body 100 is a device allowing electrons having high kinetic energy to collide with a metal target to generate an X-ray, and preferably includes an optical system such as a collimator, or the like, controlling an irradiation direction or an irradiation area of the X-ray.

The detector 140 mounted at a lower end portion of the device body 100 basically is a means for receiving the X-ray passing through the breast to obtain an image, and since the breast is put on the detector 140, the detector 140 may also serve as the support part for the object to be inspected for supporting the breast. That is, the breast is put on the detector 140 and is then pressed by the pressing pad 150, such that the breast is pressed between the detector 140 and the pressing pad 150, and the breast in a state in which it is pressed as described above is photographed by the generator 130 and the detector 140. The detector 140 generates an electric signal for each position that is in proportion to an amount of incident X-ray, and reads the electrical signal and position information and processes the read electrical signal and position information by an image processing algorithm, thereby making it possible to obtain an X-ray image of the breast. Here, a general technology content such as a direct converting scheme of obtaining the electrical signal directly from the X-ray without having a separate intermediate step, an indirect converting scheme of obtaining the electrical signal indirectly by a visible ray converted from the X-ray, or the like, depending on a scheme of converting the X-ray may be widely applied to the detector 140.

The inspection plate 160 may be included as a selective component in order to substitute for a function of the detector 140 as the support part for the object to be inspected. In the case in which the inspection plate 160 is included, the breast is pressed by the pressing pad 150 and the inspection plate 160, and the breast in this state is photographed by the generator 130 and the detector 140. Therefore, the detector 140 performs only a function of receiving the X-ray passing through the breast to obtain the image.

The mammography device configured as described above further includes a controller 300 of FIG. 7 for controlling linear movement and rotation of the device body 100. The controller 300 is a component for controlling all of the components of the mammography device, and functions of the controller 300 other than a function of controlling linear movement, and rotation of the device body 100 are the same as those of a controller of a mammography device according to the related art. That is, the function of controlling linear movement and rotation of the device body 100 may be functionally added to a controller of a mammography device that has been installed in advance. Unlike this, the controller 300 is provided in a sub-controller form to control only the linear movement and the rotation of the device body 100, and other components of the mammography device may also be controlled by a separate main controller. In the present specification, in any case, only the function of the controller 300 of controlling linear movement and rotation of the device body 100 will be described.

The controller 300 includes a mode selecting unit 320, a torque determining unit 340, and a first motor controlling unit 361, a second motor controlling unit 362, and a third motor controlling unit 363. The mode selecting unit 320 selects the following mode, that is, a craniocaudal view (CC) mode, a mediolateral oblique view (MLO) mode, a photographing angle in the case of the MLO mode, and the like, depending on an external command. The torque determining unit 340 calculates each of torques of the first motor, the second motor, and the third motor (using a relationship described below and illustrated in FIG. 8) depending on a mode selected by the mode selecting unit 320. The first motor controlling unit 361, the second motor controlling unit 362, and the third motor controlling unit 363 control each of the first motor, the second motor, and the third motor on the basis of the calculated torques of the motors to control linear movement of the device body 100 in x axis and y axis directions and rotation of the device body 100 in a z axis-direction.

The controller 300 may perform a control to simultaneously perform movement of the device body 100 in the x axis direction, ascent or descent of the device body 100, and rotation of the device body 100 by operating the first motor and the second motor for the linear movement of the device body 100 in the x axis and y axis directions and the third motor for the rotation of the device body 100 in the z axis direction together with each other.

The linear movement and the rotation of the device body 100 by the first motor, the second motor, and the third motor will be described with reference to FIG. 8. FIG. 8 is a view for describing an operation of the mammography device according to an exemplary embodiment of the present invention.

Since the object to be inspected is positioned on an upper surface of the support part 140 or 160 for the object to be inspected, it is preferable to control a linear movement distance by the rotation of the device body 100 on the basis of the center of the upper surface of the support part 140 or 160 for the object to be inspected. When the device body 100 rotates by an angle θ (in a counterclockwise direction) around the z axis, the support part 140 or 160 for the object to be inspected linearly moves by a in the x axis direction and linearly moves by b in the y axis direction. Therefore, when the device body 100 rotates by θ and at the same time, moves by a in a negative x-axis direction (leftward direction) and moves by b in a negative y-axis direction (downward direction), the center of the upper surface of the support part 140 or 160 for the object to be inspected does not move in the x axis and y axis directions, and the upper surface of the support part 140 or 160 for the object to be inspected rotates by θ. That is, the support part 140 or 160 for the object to be inspected may be maintained at an always constant position in the x axis direction and at an always constant position (that is, height) in the y axis direction. Here, when a distance from a shaft of the device body 100 to the upper surface of the support part 140 or 160 for the object to be inspected is A, values of a and b are as follows:

$$a = A^* \sin \theta$$

$$b = A - A^* \cos \theta = A(1 - \cos \theta).$$

Therefore, when the device body 100 rotates by θ and moves together with the rotation by A*sin θ and A(1−cos θ) in the leftward direction and the downward direction, the center of the upper surface of the support part 140 or 160 for the object to be inspected may be maintained at its initial position as it is.

According to the relationship as described above, the torque determining unit 340 of the controller 300 determines torques of the first motor, the second motor, and the third motor corresponding to the movement distances a and b and the rotation angle θ. Then, the first motor controlling unit 361, the second motor controlling unit 362, and the third motor controlling unit 363 receive data on the determined torques and operate the first motor, the second motor, and the third motor together with each other on the basis of the data to simultaneously perform the linear movement of the device body 100 in the x axis and y axis directions and the rotation of the device body 100 about the z axis. Here, the linear movement of the device body 100 in the x axis and y axis directions and the rotation of the device body 100 about the z axis may be performed by movement of the support column 200 by the support column moving unit, movement of the device body 100 by the device body ascending or descending unit, and rotation of the device body 100 by the device body rotating unit, respectively.

As described above, since the center of the upper surface of the support part 140 or 160 for the object to be inspected may be maintained at its initial position as it is even though the device body 100 rotates by θ, the mammography device according to an exemplary embodiment of the present invention may perform X-ray photographing at various angles without specially moving the subject. That is, a photographing time may be significantly shortened in the mammography device according to an exemplary embodiment of the present invention in which the subject does not need to move as compared with the mammography device according to the related art in which whenever a photographing angle is changed, the subject needs to move backward from the mammography device and then again enter the mammography device when a state of the mammography device is set to a corresponding orientation state, such that the mammography device according to an exemplary embodiment of the present invention may be very efficient and fatigue applied to both of the subject and a inspector may be decreased.

Meanwhile, although the support column 200 to which the device body 100 is connected moves in order the move the device body 100 in the x axis direction, in the above-mentioned exemplary embodiment, the movement of the device body 100 in the x axis direction may be implemented by fixing the support column 200 to a bottom and adding a stage movable in the x axis direction to any portion between the support column connection part 110 and the vertical connection part 120. Alternatively, the support column 200 may be fixed to the bottom, a subject stage movable in the x axis direction may be added in front of the device body 100, and the subject may be positioned in a standing or sitting state on the subject stage. It is to be noted that the subject stage needs to move by a in the x axis direction (rightward direction) (depending on the movement in the support part 140 or 160 for the object to be inspected in the x axis direction) rather than in the negative x axis direction (leftward direction) in the case in which the rotation described with reference to FIG. 8 is performed.

In a mammography device according to another exemplary embodiment of the present invention, the support column 200 may be fixed to the bottom to allow the device body 100 not to move in the x axis direction, and components related to the movement of the device body 100 in the x axis direction, that is, the first motor, the first motor controlling unit 361, and the like, may be removed. In this case, the controller 300 may perform a control to simultaneously perform ascent or descent of the device body 100 and rotation of the device body 100 by operating only the second motor provided in the device body for the linear movement of the device body 100 in the y axis direction and the third motor provided in the device body for the rotation of the device body 100 in the z axis direction with each other. Therefore, when the device body 100 rotates by θ and at the same time, moves by A(1−cos θ) in the downward direction, the center of the upper surface of the support part 140 or 160 for the object to be inspected moves in the x axis direction, but does not move in the y axis direction, such that the support part 140 or 160 for the object to be inspected may be maintained at a constant height. In the mammography device having the above-mentioned configuration, the subject has only to simply move in the rightward (or leftward) direction. Therefore, a photographing time may be significantly decreased in the mammography device having the above-mentioned configuration as compared with the mammography device according to the related art, such that the mammography device having the above-mentioned configuration may be very efficient and fatigue applied to both of the subject and the inspector may be decreased. Although movement of the subject is somewhat required, the mammography device is simpler than the mammography device according to the above mentioned exemplary embodiment, such that a cost may be decreased.

It will be obvious to those skilled in the art to which the present invention pertains that the present invention described above is not limited to the above-mentioned exemplary embodiments and the accompanying drawings, but may be variously substituted, modified, and altered without departing from the scope and spirit, of the present invention.

The invention claimed is:

1. A mammography device comprising:
    a device body movable along a vertical axis and rotatable around a first horizontal axis so as to photograph an object to be inspected by a craniocaudal view and a mediolateral oblique view;
    an X-ray generator fixed to one end portion of the device body;
    a support part for the object to be inspected including a detector fixed to another end portion of the device body and facing the X-ray generator, the support part having an upper surface with a center at an initial position;
    a second motor moving the device body along the vertical axis;
    a third motor rotating the device body around the first horizontal axis; and
    a controller controlling the second motor and the third motor,
    wherein the controller performs a control so that the third motor rotates the device body and, at the same time, the second motor moves the device body along the vertical axis together with a rotation of the device body, in order to maintain the center of the upper surface of the support part at the initial position.

2. The mammography device according to claim 1, further comprising a first motor moving the device body along a second horizontal axis perpendicular to the first horizontal axis,
    wherein the device body is movable along the second horizontal axis and the first motor is controlled by the controller, and
    the controller performs a control so that the third motor rotates the device body around the first horizontal axis and the first motor and the second motor move the device body together with a rotation of the device body in order not to move the center of the upper surface of the support part for the object to be inspected.

3. A method of controlling position alignment of a mammography device, comprising:
    providing the mammography device including a device body movable along a vertical axis and rotatable around a first horizontal axis so as to photograph an object to be inspected by a craniocaudal view and a mediolateral oblique view, an X-ray generator fixed to one end portion of the device body, and a support part for the object to be inspected including a detector fixed to another end portion of the device body and facing the X-ray generator, the support part having an upper surface with a center at an initial position; and
    rotating the device body around the first horizontal axis and, at the same time, moving the device body along the vertical axis together with a rotation of the device body in order to maintain the center of the upper surface of the support part at the initial position.

4. The method of controlling position alignment of a mammography device according to claim 3, wherein the device body is movable along a second horizontal axis perpendicular to the first horizontal axis, and
    the rotating of the device body around the first horizontal axis and the moving the device body along the vertical axis together with a rotation the device body includes rotating the device body around the first horizontal axis and moving the device body along the vertical axis and the second horizontal axis together with a rotation of the device body in order not to move the center of the upper surface of the support part for the object to be inspected.

* * * * *